(12) United States Patent
Yamashita et al.

(10) Patent No.: US 8,279,438 B2
(45) Date of Patent: Oct. 2, 2012

(54) OPTICAL MEASURING APPARATUS

(75) Inventors: Tomoyu Yamashita, Miyagi (JP); Motoki Imamura, Miyagi (JP)

(73) Assignee: Advantest Corporation, Tokyo (JP)

( * ) Notice: Subject to any disclaimer, the term of this patent is extended or adjusted under 35 U.S.C. 154(b) by 308 days.

(21) Appl. No.: 12/480,042

(22) Filed: Jun. 8, 2009

(65) Prior Publication Data
US 2010/0014079 A1 Jan. 21, 2010

(30) Foreign Application Priority Data
Jun. 18, 2008 (JP) .................................. 2008-159349

(51) Int. Cl.
*G01J 3/40* (2006.01)
(52) U.S. Cl. ..... 356/303; 356/5.07; 356/73.1; 356/5.05; 356/323
(58) Field of Classification Search .................. 356/303, 356/5.07, 484, 41, 73.1, 5.05, 323
See application file for complete search history.

(56) References Cited

U.S. PATENT DOCUMENTS

| | | | |
|---|---|---|---|
| 5,179,286 A * | 1/1993 | Akasu | 356/5.01 |
| 6,573,985 B2 * | 6/2003 | Ibukuro et al. | 356/73.1 |
| 6,690,001 B2 * | 2/2004 | Jiang et al. | 324/244.1 |
| 2007/0171401 A1 | 7/2007 | Ukita | |
| 2008/0165355 A1 | 7/2008 | Yasui et al. | |

FOREIGN PATENT DOCUMENTS
WO 2006/092874 9/2006
* cited by examiner

*Primary Examiner* — Gregory J Toatley
*Assistant Examiner* — Iyabo S Alli
(74) *Attorney, Agent, or Firm* — Greenblum & Bernstein, P.L.C.

(57) ABSTRACT

An object is to enable a change in a frequency for which an electric signal based on an optical signal is measured by a spectrum analyzer. An optical measurement device includes a first photoconductive switch that receives predetermined pulse light from a first laser light source, and outputs terahertz light having the same repetition frequency as the repetition frequency of the predetermined pulse light. The optical measurement device also includes a second photoconductive switch that receives the terahertz light and a sampling light pulse, and outputs a signal corresponding to a power of the terahertz light at a time point when the sampling light pulse is received. The optical measurement device further includes an RF spectrum analyzer that measures a magnitude of the signal corresponding to a measured frequency that changes over time, an optical coupler that outputs a simultaneous light pulse when the predetermined pulse light and the sampling light pulse are simultaneously input, a photo detector that converts the simultaneous light pulse into an electric signal as a trigger signal, and an optical delay circuit that delays the trigger signal.

9 Claims, 8 Drawing Sheets

OPTICAL MEASURING APPARATUS

BACKGROUND ART

1. Field of the Invention
The present invention relates to measurement of light.

2. Description of the Prior Art
There has conventionally been known a method for measuring a device under test by a terahertz detector receiving terahertz light A (in a form of pulse) which has been fed from a terahertz emitter to the device under test, and has transmitted through the device under test, and light B having the pulse period which is slightly different from the pulse period of terahertz light A (refer to ABSTRACT of Patent Document 1, for example).

When the repetition frequency of the terahertz light A is $f_A$ and the repetition frequency of the light B is $f_B$, a time required for measuring one period of the light pulse which has transmitted through the device under test is represented as:

$$1/(f_A-f_B)[s]$$

Moreover, a measurement of a signal using a spectrum analyzer is widely known. The spectrum analyzer measures the power of a signal for respective frequencies. The frequency at which the spectrum analyzer carries out the measurement changes over time. In other words, the spectrum analyzer sweeps the frequency for the measurement.

(Patent Document 1) WO 2006/092874, Pamphlet

Then, it is conceivable to measure the signal detected by the terahertz detector by the spectrum analyzer. The frequency for which the spectrum analyzer carries out the measurement is represented as $$f_s+n \cdot S/(f_A-f_B)[Hz]$$

where $f_s$ [Hz] is a frequency from which the spectrum analyzer starts the sweep, and S [Hz/s] is a velocity of the change in the frequency for which the spectrum analyzer carries out the measurement (it should be noted that n is zero or a positive integer).

SUMMARY OF THE INVENTION

However, the measurement by the spectrum analyzer cannot be carried out if a frequency $f_0$ for which the measurement is intended is as follows:

$$f_s+n0 \cdot S/(f_A-f_B) \leq f_0 < f_s+(1+n0) \cdot S/(f_A-f_B)$$

(n0 is 0 or one of positive integers)

It is therefore an object of the present invention to enable a change in a frequency for which an electric signal based on an optical signal is measured by a spectrum analyzer.

According to the present invention, an optical measurement device includes: a detected light pulse output unit that receives a predetermined pulse light, and outputs a detected light pulse having the same repetition frequency as the repetition frequency of the predetermined pulse light; a signal output device that receives the detected light pulse and a sampling light pulse, and outputs a signal corresponding to a power of the detected light pulse upon the reception of the sampling light pulse; a frequency spectrum measurement device that measures a magnitude of the signal corresponding to a measured frequency which changes over time; a simultaneous light pulse output unit that outputs a simultaneous light pulse when the predetermined pulse light and the sampling light pulse are simultaneously input; a trigger signal generation unit that converts the simultaneous light pulse into an electric signal as a trigger signal; and a trigger signal delay unit that delays the trigger signal, wherein: the repetition frequency of the detected light pulse and the repetition frequency of the sampling light pulse are different from each other; and the measured frequency starts to change from a time point when the trigger signal is fed to the frequency spectrum measurement device.

According to the thus constructed optical measurement device, a detected light pulse output unit receives a predetermined pulse light, and outputs a detected light pulse having the same repetition frequency as the repetition frequency of the predetermined pulse light. A signal output device receives the detected light pulse and a sampling light pulse, and outputs a signal corresponding to a power of the detected light pulse upon the reception of the sampling light pulse. A frequency spectrum measurement device measures a magnitude of the signal corresponding to a measured frequency which changes over time. A simultaneous light pulse output unit outputs a simultaneous light pulse when the predetermined pulse light and the sampling light pulse are simultaneously input. A trigger signal generation unit converts the simultaneous light pulse into an electric signal as a trigger signal. A trigger signal delay unit delays the trigger signal.

Furthermore, the repetition frequency of the detected light pulse and the repetition frequency of the sampling light pulse are different from each other, and the measured frequency starts to change from a time point when the trigger signal is fed to the frequency spectrum measurement device.

According to the optical measurement device of the present invention, the trigger signal delay unit may delay the simultaneous light pulse, and feed the delayed simultaneous light pulse to the trigger signal generation unit.

According to the optical measurement device of the present invention, the trigger signal delay unit may be arranged inside the frequency spectrum measurement device.

According to the optical measurement device of the present invention, the trigger signal delay unit may delay the sampling light pulse, and feed the delayed sampling light pulse to the simultaneous light pulse output unit.

According to the optical measurement device of the present invention, a quantity of the change in the measured frequency from the time point when the trigger signal is fed to the frequency spectrum measurement device may be proportional to a period which has elapsed from the time point.

According to the optical measurement device of the present invention, the detected light pulse output unit and the signal output device may be photoconductive switches.

According to the optical measurement device of the present invention, the detected light pulse may be terahertz light.

According to the optical measurement device of the present invention, the signal may be a current.

According to the optical measurement device of the present invention, the detected light pulse output unit may be a non-linear optical crystal; and the signal output device may be an electro-optic crystal.

BRIEF DESCRIPTION OF THE DRAWINGS

FIGS. 3(a) to 3(d) are time charts, in which FIG. 3(a) is that for the terahertz light L1, FIG. 3(b) is that for the sampling light pulse L2, FIG. 3(c) is that for the trigger signal EXT (assuming that $t_d=0$), and FIG. 3(d) is that for the trigger signal EXT;

BEST MODE FOR CARRYING OUT THE INVENTION

A description will now be given of an embodiment of the present invention with reference to drawings.

Figure 1:
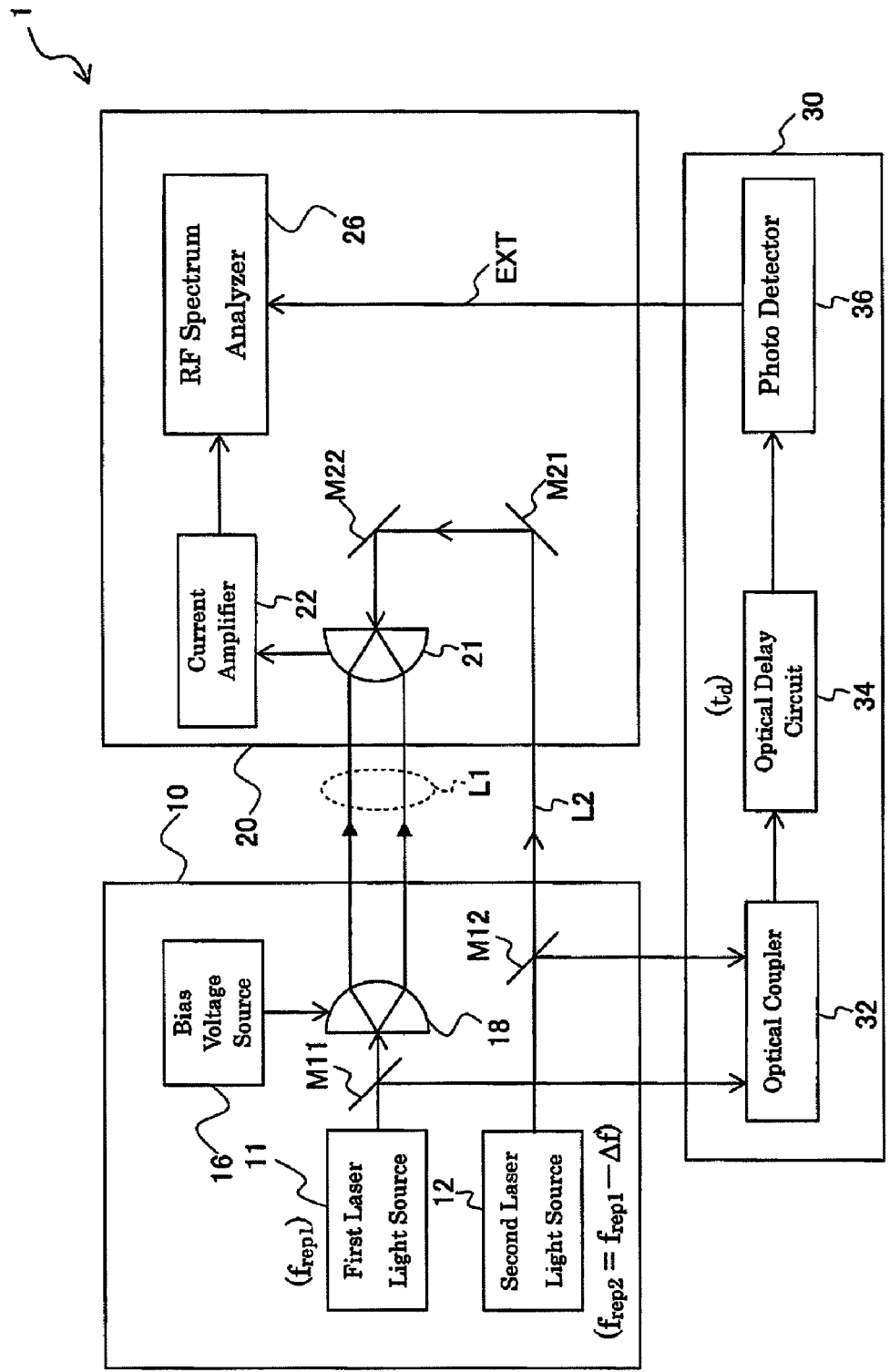
FIG. 1 is a block diagram showing a configuration of an optical measurement device 1 according an embodiment of the present invention.

FIG. 1 is a block diagram showing a configuration of an optical measurement device 1 according the embodiment of the present invention. The optical measurement device 1 includes a light output device 10, a light reception device 20, and a trigger signal adding device 30.

The light output device 10 includes a first laser light source 11, a second laser light source 12, a bias voltage source 16, a photoconductive switch (detected light pulse output unit) 18, and half mirrors M11 and M12.

The first laser light source 11 outputs laser pulse light (predetermined pulse light) having a pulse width of several tens of femtoseconds and having a wavelength in a near infrared area. The laser pulse light is split by the half mirror M11 to light fed to the trigger signal adding device 30 and the light fed to the photoconductive switch 18. It should be noted that the repetition frequency of the laser pulse light is $f_{rep1}$.

The second laser light source 12 is a laser light source which outputs a sampling light pulse L2. The repetition frequency of the sampling light pulse L2 is $f_{rep2}$ ($=f_{rep1}-\Delta f$). It should be noted that $\Delta f>0$. The sampling light pulse L2 is split by the half mirror M12 to light fed to the light reception device 20 and light fed to the trigger signal adding device 30.

The bias voltage source 16 feeds a DC voltage to the photoconductive switch 18.

The photoconductive switch (detected light pulse output unit) 18, upon receiving the laser pulse light (predetermined pulse light) from the laser light source 11, outputs terahertz light L1. The structure of the photoconductive switch 18 is widely known, and a description thereof, therefore, is omitted. The terahertz light (detected light pulse) L1 output from the photoconductive switch 18 is a light pulse, and the repetition frequency thereof is $f_{rep1}$, which is the same as the repetition frequency of the laser pulse light.

The light reception device 20 includes a photoconductive switch (signal output device) 21, a current amplifier 22, an RF spectrum analyzer (frequency spectrum measurement device) 26, and mirrors M21 and M22.

The photoconductive switch (signal output device) 21 receives the terahertz light L1. It is conceivable that the photoconductive switch 21 receives the terahertz light L1 via a certain device under test. Moreover, the sampling light pulse L2 is led by the mirrors M21 and M22 to the photoconductive switch 21. Thus, the photoconductive switch 21 receives the sampling light pulse L2. The photoconductive switch 21, upon receiving the sampling light pulse L2, outputs a signal corresponding to the power of the terahertz light L1. It should be noted that the signal output from the photoconductive switch 21 is a current. Moreover, the structure of the photoconductive switch 18 is widely known, and a description thereof, therefore, is omitted.

The current amplifier 22 amplifies the current generated on the photoconductive switch 21.

The RF spectrum analyzer (frequency spectrum measurement device) 26 measures a magnitude of the signal corresponding to a measured frequency which changes over time. The change of the measured frequency over time implies a sweep. The sweep starts from a time point when a trigger signal EXT is fed to the RF spectrum analyzer 26.

Figure 2:
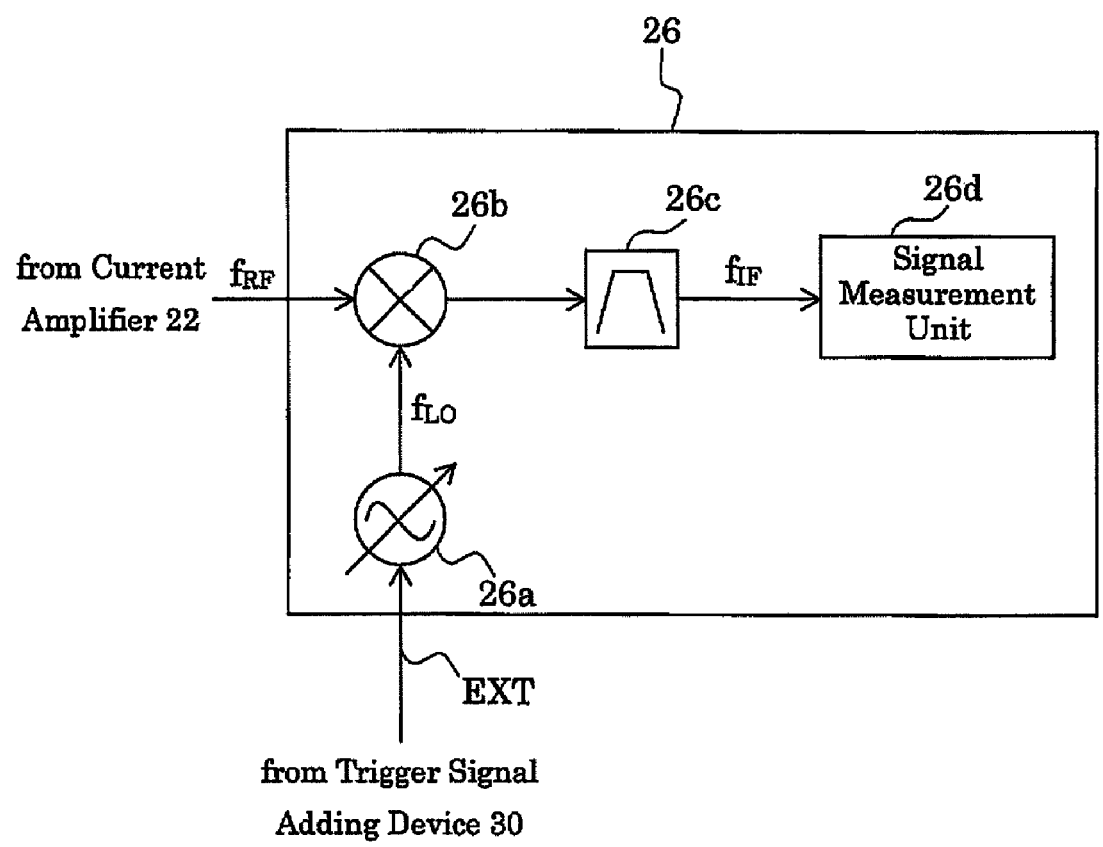
FIG. 2 is a block diagram showing a configuration of a RF spectrum analyzer 26.

FIG. 2 is a block diagram showing a configuration of the RF spectrum analyzer 26. The RF spectrum analyzer 26 includes a local signal source 26a, a mixer 26b, a band-pass filter 26c, and a signal measurement unit 26d. Though the RF spectrum analyzer 26 includes only one mixer in FIG. 2, it is widely known that the RF spectrum analyzer 26 may include multiple mixers.

The local signal source 26a outputs a local signal (frequency $f_{LO}$). The frequency $f_{LO}$ changes over time. In other words, $f_{LO}=f_{LOS}+S \cdot t_p$ (where $f_{LOS}$ is an initial value of the local frequency $f_{LO}$ [Hz], S is a velocity of the sweep (Hz/second), $t_p$ is a period [second] which has elapsed since the local signal source 26a receives the trigger signal EXT.

The mixer 26b multiplies the current output from the current amplifier 22 and the local signal.

The band-pass filter 26c extracts a signal with a predetermined frequency $f_{IF}$ from the output of the mixer 26b.

The signal measurement unit 26d measures the magnitude (may also measure the phase) of the output from the band-pass filter 26c. The signal measured by the signal measurement unit 26d is a component with a frequency $f_{RF}$ out of the current output from the current amplifier 22. It should be noted that $f_{RF}=f_{IF}+f_{LO}=f_{IF}+f_{LOS}+S \cdot t_p$. On this occasion, when $f_{IF}+f_{LOS}$ is set to $f_S$, $f_{RF}=f_S+S \cdot t_p$. The frequency $f_{RF}$ is the measured frequency described before. The amount of the change $S \cdot t_p$ of the frequency $f_{RF}$ from the time point when the trigger signal EXT is fed to (the local signal source 26a of) the RF spectrum analyzer 26 is proportional to the period $t_p$ which has elapsed from the time point when the trigger signal EXT is fed to (the local signal source 26a of) the RF spectrum analyzer 26.

The trigger signal adding device 30 includes an optical coupler (simultaneous light pulse output unit) 32, an optical delay circuit (trigger signal delay unit) 34, and a photo detector (trigger signal generation unit) 36.

The optical coupler (simultaneous light pulse output unit) 32 outputs a simultaneous light pulse when the laser pulse light and the sampling light pulse L2 are input at the same time.

The optical delay circuit (trigger signal delay unit) 34 delays the simultaneous light pulse, and feeds the delayed simultaneous light pulse to the photo detector 36. As a result, it is possible to delay the trigger signal EXT more than a case in which the optical delay circuit 34 is not provided. It should be noted that a period by which the optical delay circuit 34 delays the trigger signal EXT is $t_d$.

The photo detector (trigger signal generation unit) 36 receives the simultaneous light pulse via the optical delay circuit 34, converts the simultaneous light pulse into an electric signal, and feeds the electric signal as the trigger signal EXT to the RF spectrum analyzer 26.

A description will now be given of an operation of the embodiment of the present invention.

The laser light source 11 of the light output device 10 outputs the laser pulse light. The laser pulse light transmits through the half mirror M11, and is fed to the photoconductive switch 18. To the photoconductive switch 18, the DC voltage is fed by the bias voltage source 16. On this occasion, if the laser pulse light is fed to the photoconductive switch 18, the terahertz light L1 is output from the photoconductive switch 18. The terahertz light L1 is fed to the photoconductive switch 21 of the light reception device 20.

The second laser light source 12 outputs the sampling light pulse L2. The sampling light pulse L2 transmits though the half mirror M12, and is further reflected by the mirrors M21 and M22, and is fed to the photoconductive switch 21.

The photoconductive switch 21, upon receiving the sampling light pulse L2, outputs a current corresponding to the power of the terahertz light L1. This current is amplified by the current amplifier 22, and is measured by the RF spectrum analyzer 26.

Moreover, the laser pulse light is reflected by the half mirror M11, and is fed to the optical coupler 32 of the trigger signal adding device 30. The sampling light pulse L2 is reflected by the half mirror M12, and is fed to the optical coupler 32. The optical coupler 32 outputs the simultaneous light pulse when the laser pulse light and the sampling light pulse L2 are input at the same time.

The simultaneous light pulse is delayed by the optical delay circuit 34 by the period $t_d$, and is fed to the photo detector 36. The photo detector 36 converts the simultaneous light pulse into the electric signal, and feeds the electric signal as the trigger signal EXT to the RF spectrum analyzer 26. When the trigger signal EXT is fed to (the local signal source 26a of) the RF spectrum analyzer 26, the sweep starts.

Figure 3:
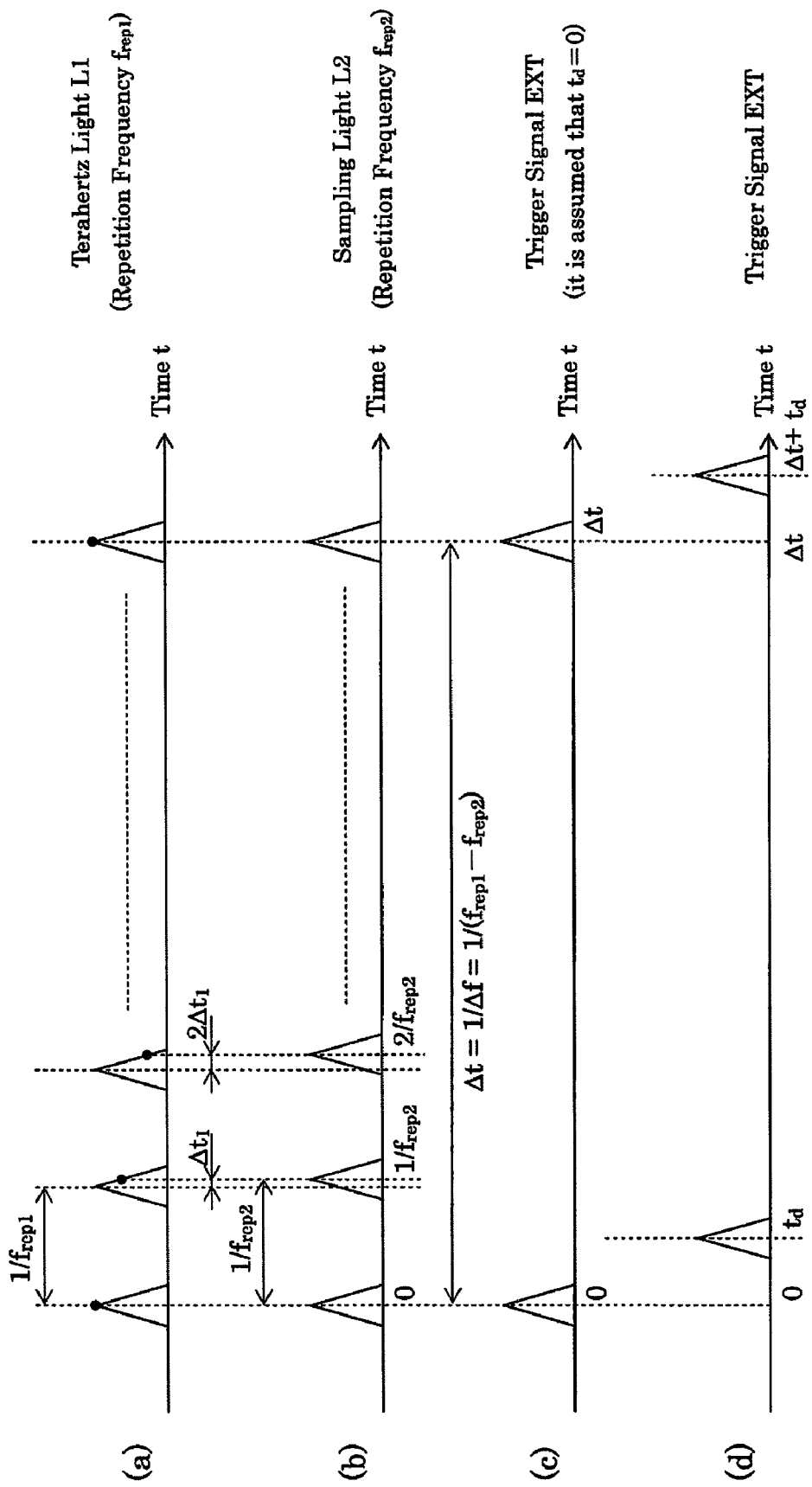

FIGS. 3(a) to 3(d) are time charts, in which FIG. 3(a) is that for the terahertz light L1, FIG. 3(b) is that for the sampling light pulse L2, FIG. 3(c) is that for the trigger signal EXT (assuming that $t_d=0$), and FIG. 3(d) is that for the trigger signal EXT. It should be noted that there is no time difference between the laser pulse light and the terahertz light L1 for the sake of illustration.

The photoconductive switch 21 outputs the current corresponding to the power of the terahertz light L1 when the optical power of the pulse of the sampling light pulse L2 takes the maximum. For example, the photoconductive switch 21 outputs the current corresponding to the power of the terahertz light L1 at time points t=0, $1/f_{rep2}$, $2/f_{rep2}$, . . . . In other words, the photoconductive switch 21 outputs the current corresponding to the power of the terahertz light L1 at time points (0, $\Delta t_1$, $2\Delta t_1$, . . . ) displaced respectively by integer multiples of $\Delta t_1 (=1/f_{rep2}-1/f_{rep1})$ from the time point when the power of the terahertz light L1 takes the maximum. The photoconductive switch 21 outputs the current corresponding to the power of the terahertz light L1 when the displacement from the time point maximizing the power of the terahertz light L1 becomes $1/f_{rep1}$ in time (refer to a pulse on the right end in FIG. 3(a)). At this time point, the measurement of the pulse of the terahertz light L1 for one cycle has been completed. The period $\Delta t$ required for the completion of measurement for one cycle of the pulse of the terahertz light L1 is represented as $$t=1/\Delta f=1/(f_{rep1}-f_{rep2}).$$

On this occasion, if it is assumed that $t_d=0$ (corresponding to a case without the optical delay circuit 34), the trigger signal EXT is output when t=0 and t=$\Delta t$ (refer to FIG. 3(c)). However, actually $t_d>0$, and the trigger signal EXT is thus output at t=$t_d$ and t=$\Delta t+t_d$ (refer to FIG. 3(d)).

Figure 4:
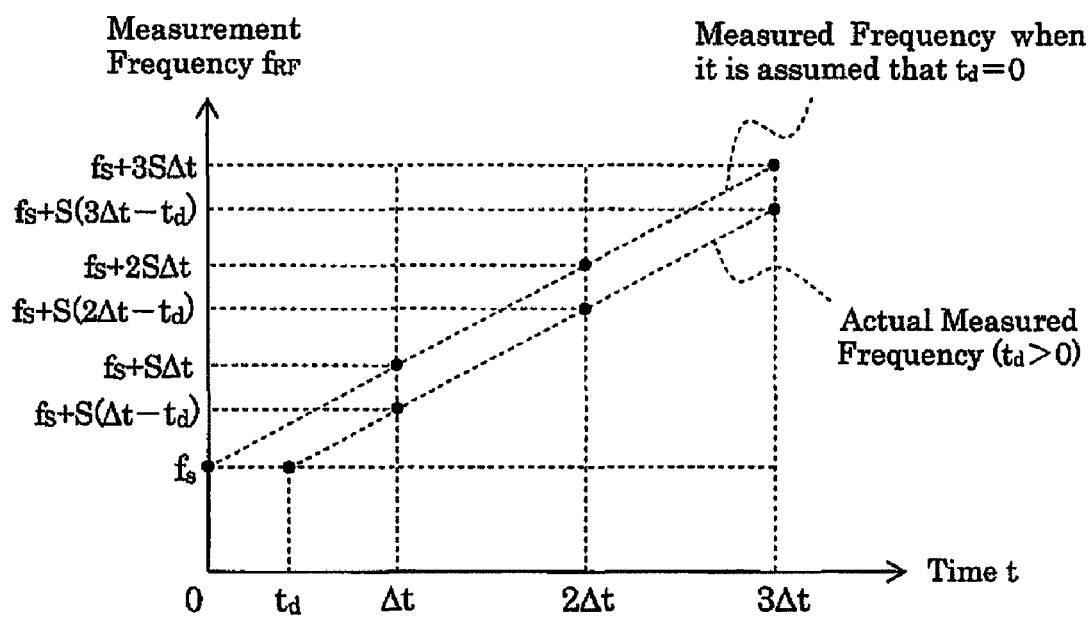
FIG. 4 shows the measurement frequency $f_{RF}$ when it is assumed that $t_d=0$ (which corresponds to the case without optical delay circuit 34), and the actual measured frequency $f_{RF}(t_d>0)$.

FIG. 4 shows the measurement frequency $f_{RF}$ when it is assumed that $t_d=0$ (which corresponds to the case without optical delay circuit 34), and the actual measured frequency $f_{RF}$ ($t_d>0$). Since the current output from the current amplifier 22 is measured at the time points t=0, $\Delta t$, $2\Delta t$, $3\Delta t$, . . ., the measured frequencies $f_{RF}$ assuming that $t_d=0$ are represented as $f_S$, $f_S+S\Delta t$, $f_S+2S\Delta t$, $f_S+3S\Delta t$, . . . by assigning 0, $\Delta t$, $2\Delta t$, $3\Delta t$, . . . to $t_p$ of $f_{RF}=f_S+S \cdot t_p$.

However, actually $t_d>0$. Then, the period which has elapsed since the local signal source 26a receives the trigger signal EXT is represented as t−$t_d$. Thus, the measured frequency $f_{RF}$ is represented, by assigning 0, $\Delta t-t_d$, $2\Delta t-t_d$, $3\Delta t-t_d$, . . . to $t_p$ of $f_{RF}=f_S+S \cdot t_p$, as:

$$f_S, f_S+S(\Delta t-t_d), f_S+S(2\Delta t-t_d), f_S+S(3\Delta t-t_d),$$

Without the optical delay circuit 34, since the measured frequency $f_{RF}$ is represented as $f_S$, $f_S+S\Delta t$, $f_S+2S\Delta t$, $f_S+3S\Delta t$, . . . , if the frequency $f_0$ to be measured is $f_S+2S\Delta t<f_0<f_S+3S\Delta t$, for example, the measurement is impossible.

However, according to the embodiment of the present invention, it is possible to, by properly adjusting $t_d$, to attain $f_0=f_S+S(3\Delta t-t_d)$. In other words, the measured frequency $f_{RF}$ can be set between $f_S+2S\Delta t$ and $f_S+3S\Delta t$. As a result, when the electric signal based on the light signal is measured by the RF spectrum analyzer 26, the frequency $f_{RF}$ to be measured can be properly changed.

Though the description has been given of the case in which the optical delay circuit (trigger signal delay unit) 34 is provided between the optical coupler 32 and the photo detector 36, the trigger signal delay unit may be provided at other location.

Figure 5:
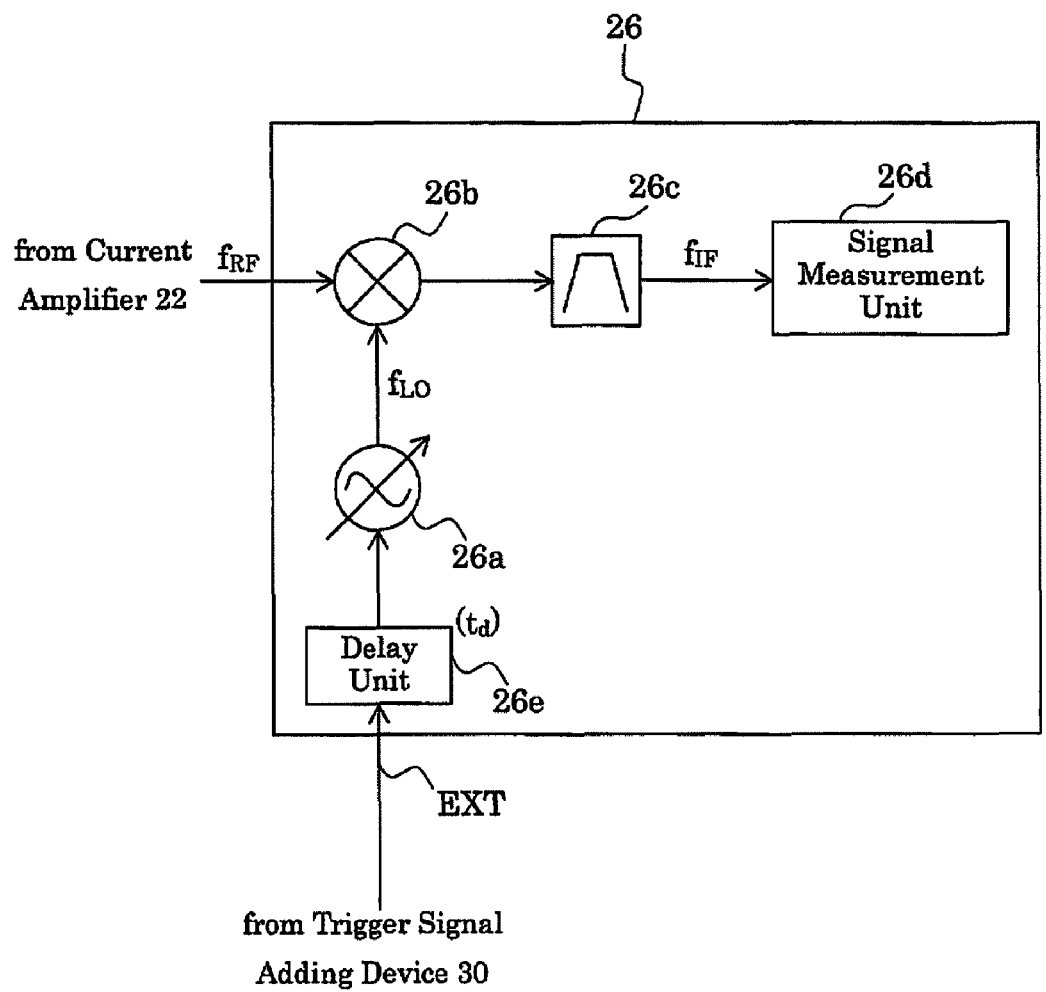
FIG. 5 is a block diagram showing a configuration of the RF spectrum analyzer 26 when a delay unit (trigger signal delay unit) 26e is provided inside the RF spectrum analyzer 26.

FIG. 5 is a block diagram showing a configuration of the RF spectrum analyzer 26 when a delay unit (trigger signal delay unit) 26e is provided inside the RF spectrum analyzer 26. The delay unit 26e delays the trigger signal EXT by the period $t_d$, and feeds the delayed trigger signal EXT to the local signal source 26a.

Figure 6:
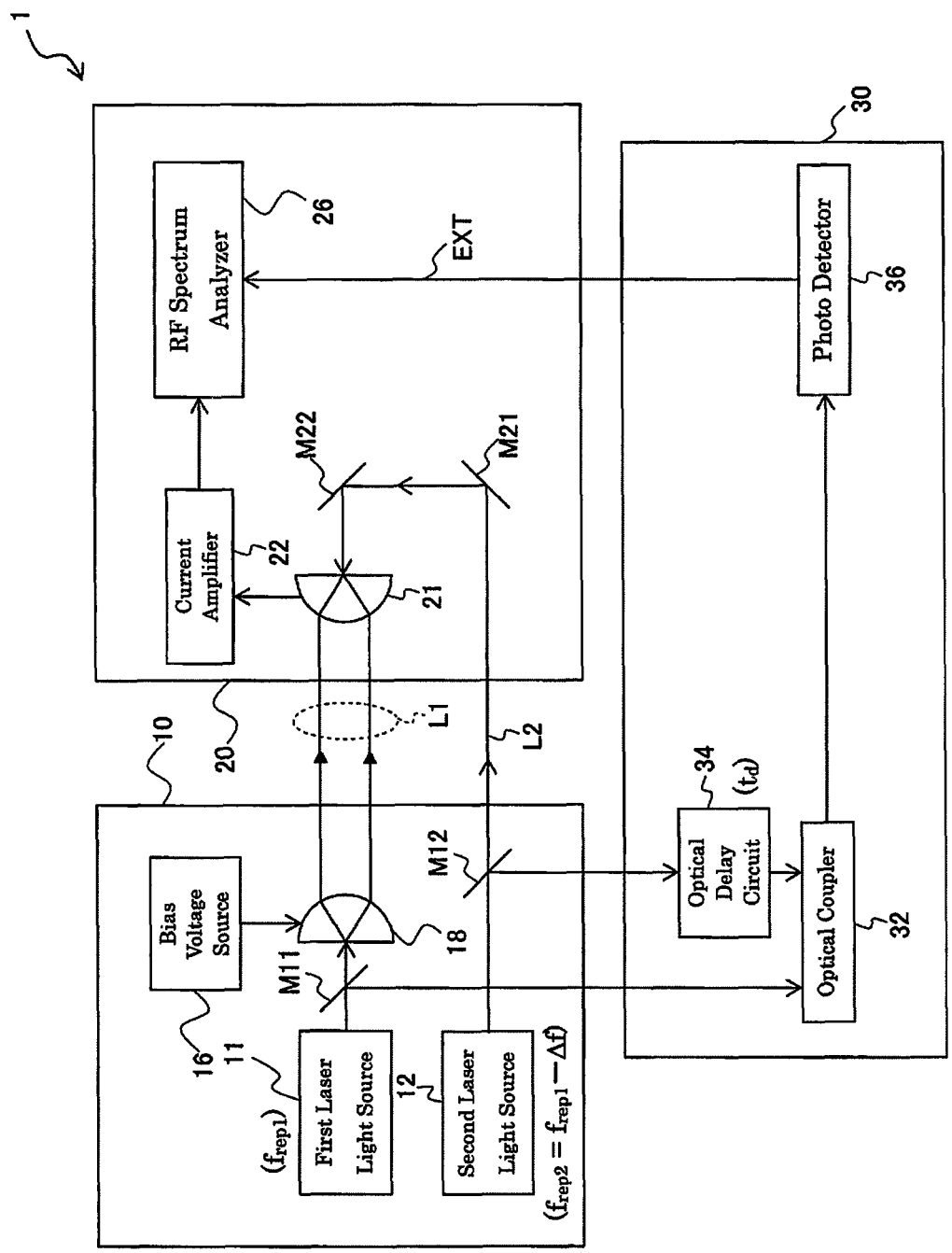
FIG. 6 is a block diagram showing a configuration of the optical measurement device 1 when the optical delay circuit (trigger signal delay unit) 34 is provided between the optical coupler 32 and the half mirror M12.

FIG. 6 is a block diagram showing a configuration of the optical measurement device 1 when the optical delay circuit (trigger signal delay unit) 34 is provided between the optical coupler 32 and the half mirror M12. The optical delay circuit 34 delays the sampling light pulse L2 by the period $t_d$, and feeds the delayed sampling light pulse L2 to the optical coupler 32.

It should be noted that the description has been given of the example in which the photoconductive switches 18 and 21 are used as the detected light pulse output unit and the signal output device. However, a non-linear optical crystal may be used as the detected light pulse output unit, and an electro-optic crystal may be used as the signal output device.

Figure 7:
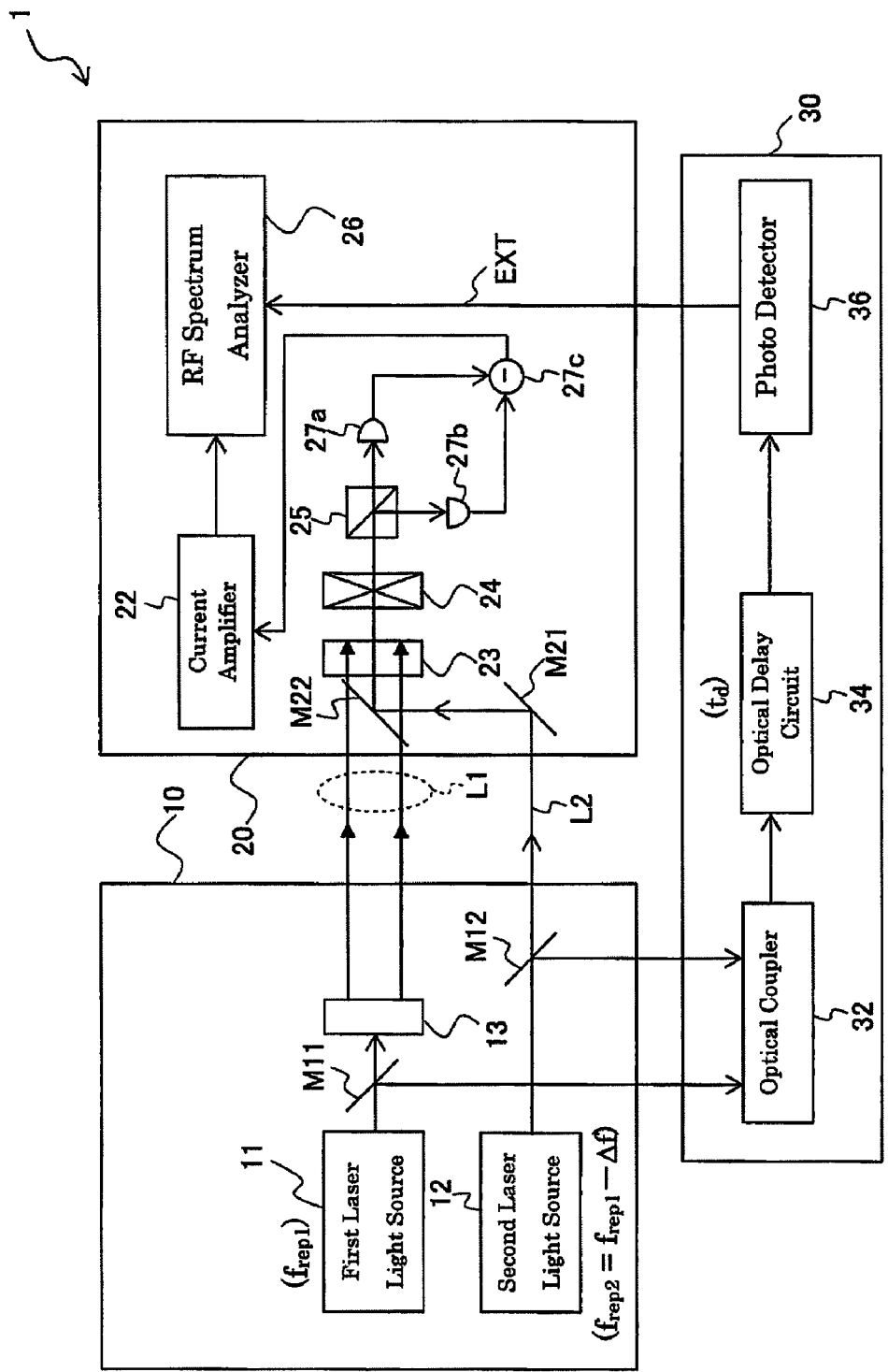
FIG. 7 is a block diagram showing a configuration of the optical measurement device 1 according the embodiment of the present invention when a non-linear optical crystal is used.

FIG. 7 is a block diagram showing a configuration of the optical measurement device 1 according the embodiment of the present invention when a non-linear optical crystal is used. The optical measurement device 1 includes the light output device 10, the light reception device 20, and the trigger signal adding device 30.

The light output device 10 includes the first laser light source 11, the second laser light source 12, a non-linear optical crystal 13, and the half mirrors M11 and M12. The first laser light source 11, the second laser light source 12, and the half mirrors M11 and M12 are the same as those of the optical measurement device 1 described referring to FIG. 1, and a description thereof, therefore, is omitted.

The non-linear optical crystal (detected light pulse output unit) 13, upon receiving the laser pulse light (predetermined pulse light) from the laser light source 11, outputs the terahertz light L1. The non-linear optical crystal 13 is DAST or ZnTe, for example. The terahertz light (detected light pulse) L1 output form the non-linear optical crystal 13 is a light pulse, and the repetition frequency thereof is $f_{rep1}$, which is the same as the repetition frequency of the laser pulse light.

The light reception device 20 includes the current amplifier 22, an electro-optic crystal (signal output device) 23, a quarter-wave plate 24, a polarization beam splitter 25, the RF spectrum analyzer (frequency spectrum measurement device) 26, photo detectors 27a and 27b, a subtractor 27c, and the mirrors M21 and M22.

The electro-optic crystal (signal output device) 23 receives the terahertz light L1. The electro-optic crystal 23 is DAST, ZnTe, or GaAS, for example. It is conceivable that the electro-optic crystal 23 receives the terahertz light L1 via a certain device under test. Moreover, the sampling light pulse L2 is led by the mirrors M21 and M22 to the electro-optic crystal 23. Thus, the electro-optic crystal 23 receives the sampling light pulse L2. Upon the electro-optic crystal 23 receiving the sampling light pulse L2, according to the power of the terahertz light L1, a birefringence change of the electro-optic crystal 23 occurs. A polarization state of the sampling light pulse L2 which has transmitted through the electro-optic crystal 23 changes due to influence of the birefringence change which has occurred in the electro-optic crystal 23.

In other words, the electro-optic crystal (signal output device) 23, upon receiving the sampling light pulse L2, outputs a signal (sampling light pulse L2) the polarization state of which has changed according to the power of the terahertz light L1.

The signal (sampling light pulse L2) output from the electro-optic crystal 23 is fed via the quarter-wave plate 24 (widely-known quarter-wave plate, and hence a description thereof is omitted) to the polarization beam splitter 25. The signal is branched into two beams by the polarization beam splitter 25, and is converted by the photo detectors 27a and 27b into electric signals. The two electric signals output from the photo detectors 27a and 27b are fed to the subtractor 27c, and a difference therebetween is obtained. An output from the subtractor 27c is fed to the current amplifier 22.

The current amplifier 22 and the RF spectrum analyzer 26 are the same as those of the optical measurement device 1 described referring to FIG. 1, and a description thereof, therefore, is omitted.

An operation for the case in which the non-linear optical crystal is used in the optical measurement device 1 according to the embodiment of the present invention is the same as the operation of the optical measurement device 1 described referring to FIG. 1, and a description thereof, therefore, is omitted.

Moreover, though the description has been given of the case in which the optical delay circuit (trigger signal delay unit) 34 is provided between the optical coupler 32 and the photo detector 36 referring to FIG. 7, the trigger signal delay unit may be provided at other location as described above.

For example, referring to FIG. 5, the delay unit (trigger signal delay unit) 26e may be provided inside the RF spectrum analyzer 26. In this case, the delay unit 26e delays the trigger signal EXT by the period $t_d$, and feeds the delayed trigger signal EXT to the local signal source 26a.

Figure 8:
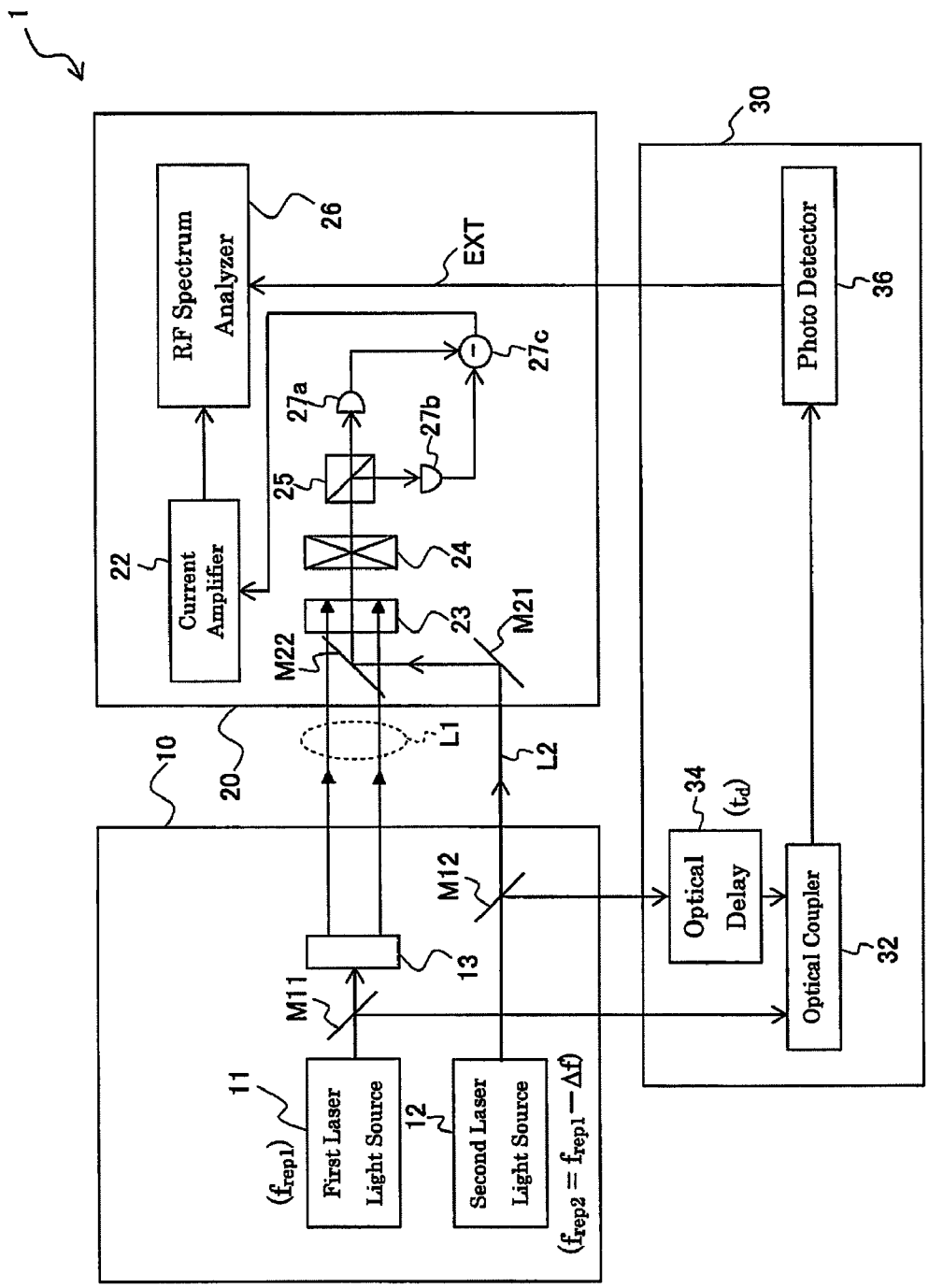
FIG. 8 is a block diagram showing a configuration of the optical measurement device 1 when the optical delay circuit (trigger signal delay unit) 34 is provided between the optical coupler 32 and the half mirror M12 for the case in which the non-linear optical crystal is used.

FIG. 8 is a block diagram showing a configuration of the optical measurement device 1 when the optical delay circuit (trigger signal delay unit) 34 is provided between the optical coupler 32 and the half mirror M12 for the case in which the non-linear optical crystal is used.

For example, the optical delay circuit (trigger signal delay unit) 34 may be provided between the optical coupler 32 and the half mirror M12 referring to FIG. 8. The optical delay circuit 34 delays the sampling light pulse L2 by the period $t_d$, and feeds the delayed sampling light pulse L2 to the optical coupler 32.

The invention claimed is:

1. An optical measurement device, comprising:
   a detected light pulse outputter that receives a predetermined pulse light, and outputs a detected light pulse having a same repetition frequency as a repetition frequency of the predetermined pulse light;
   a signal outputter that receives the detected light pulse and a sampling light pulse, and outputs a signal corresponding to a power of the detected light pulse upon a reception of the sampling light pulse;
   a frequency spectrum measurer that measures a magnitude of a signal corresponding to a measured frequency which changes over time;
   a simultaneous light pulse outputter that outputs a simultaneous light pulse when the predetermined pulse light and the sampling light pulse are simultaneously input;
   a trigger signal generator that converts the simultaneous light pulse into an electric signal as a trigger signal; and
   a trigger signal delayer that delays the trigger signal, wherein:
   the repetition frequency of the detected light pulse and a repetition frequency of the sampling light pulse are different from each other; and
   the measured frequency starts to change from a time point when the trigger signal is fed to the frequency spectrum measurer.

2. The optical measurement device according to claim 1, wherein the trigger signal delayer delays the simultaneous light pulse, and feeds the delayed simultaneous light pulse to the trigger signal generator.

3. The optical measurement device according to claim 1, wherein the trigger signal delayer is arranged inside the frequency spectrum measurer.

4. The optical measurement device according to claim 1, wherein the trigger signal delayer delays the sampling light pulse, and feeds the delayed sampling light pulse to the simultaneous light pulse outputter.

5. The optical measurement device according to claim 1, wherein a quantity of the change in the measured frequency from the time point when the trigger signal is fed to the frequency spectrum measurer is proportional to a period which has elapsed from the time point.

6. The optical measurement device according to claim 1, wherein the detected light pulse outputter and the signal outputter are photoconductive switches.

7. The optical measurement device according to claim 1, wherein the detected light pulse is terahertz light.

8. The optical measurement device according to claim 1, wherein the signal is a current.

9. The optical measurement device according to claim 1, wherein:
   the detected light pulse outputter is a non-linear optical crystal; and
   the signal outputter is an electro-optic crystal.

* * * * *